Figure 3:
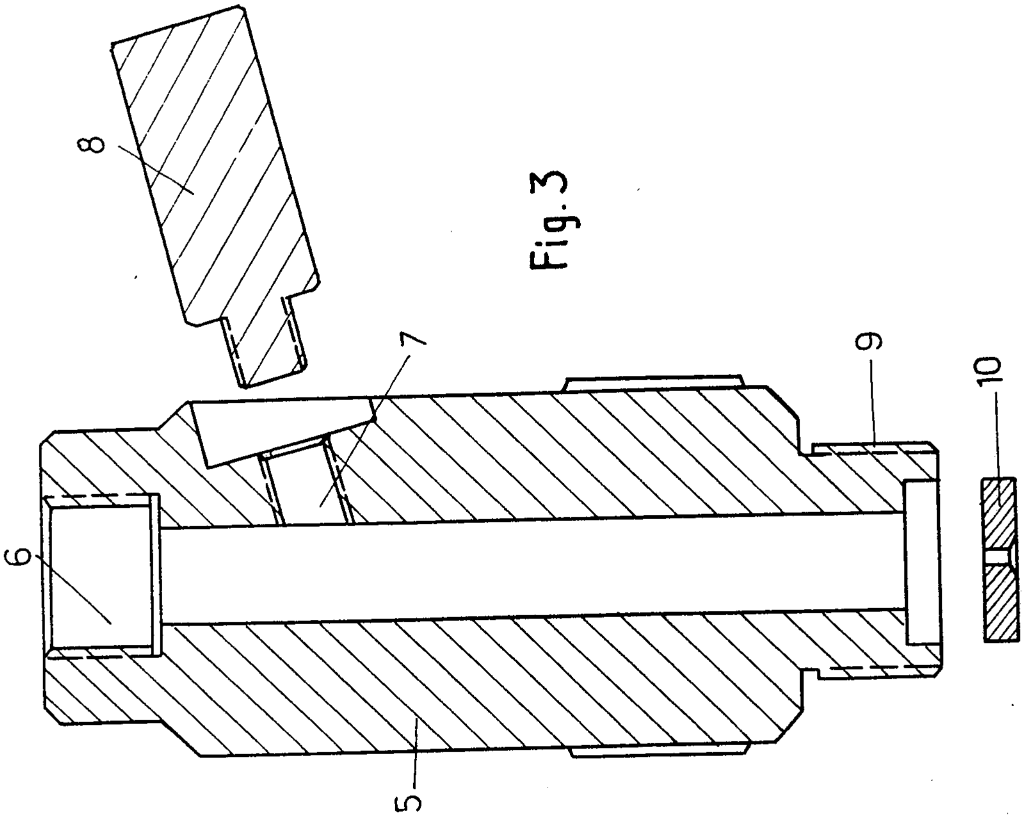

United States Patent [19]

Cazorla et al.

[11] 4,017,602

[45] Apr. 12, 1977

[54] PROCESS FOR PREPARING PRODUCTS FOR USE IN AEROSOL FORM

[75] Inventors: Jean Cazorla; Yves Tillon, both of Bernay, France

[73] Assignee: Roger & Gallet, Paris, France

[22] Filed: Aug. 15, 1975

[21] Appl. No.: 605,089

[30] Foreign Application Priority Data

Aug. 28, 1974 France .............................. 74.29386

[52] U.S. Cl. ...................................... 424/44; 195/1; 195/54; 195/109; 252/90; 252/305; 53/36

[51] Int. Cl.$^2$ ............................................ A61L 9/04

[58] Field of Search ........................... 195/1, 54–60, 195/99–102, 107, 109, 136, 137; 426/8, 116; 424/44; 252/305; 53/36, 21 R, 21 F

[56] References Cited

UNITED STATES PATENTS

| | | | |
|---|---|---|---|
| 3,480,185 | 11/1969 | Steinberg et al. | 252/305 X |
| 3,900,571 | 8/1975 | Johnson | 426/15 |

*Primary Examiner*—Lionel M. Shapiro
*Attorney, Agent, or Firm*—William Anthony Drucker

[57] ABSTRACT

Process for the preparation of products for use in aerosol form comprising the preparation of a base composition, the introduction of this composition into an aerosol container and the use of a propellant, wherein the composition is previously inoculated with micro-organisms able to bring about fermentation with the giving off within the container of carbondioxide gas which serves as the propellant.

Application to the preparation of cosmetics.

13 Claims, 3 Drawing Figures

PROCESS FOR PREPARING PRODUCTS FOR USE IN AEROSOL FORM

The present invention relates to the preparation of products which are to be used as aerosols.

These are more particularly cosmetic products, hygienic and sanitary articles and pharmaceutical or para-pharmaceutical products for external use as well as foodstuffs. They can have the consistency of a paste, cream or liquid.

In addition to their extremely varied active principles, conventional cosmetics most frequently use chemical preserving agents (antioxidants, bactericides, bacteriostatics, fungicides and fungistatics) which to a greater or lesser extent are toxic or aggressive to the skin. Their use in aerosols in certain cases makes it unnecessary to use an antioxidant if the residual air is purged from the container by means of the propellant. However, the propellant is a gas having a chemical origin such as, for example, nitrogen or a chlorofluorinated derivative having no microbicidal properties, and it is therefore necessary to add agents which contain the latter.

Disadvantages of the same type occur with numerous products other than cosmetics used in aerosol form.

The invention aims at eliminating these disadvantages and obtaining an effective stabilization of the product used in aerosol form generally without using a chemical preservative, whilst improving the stability, microbiological purity and in certain cases the biologically active qualities of the product used in this way.

The invention has for its object a process for the preparation of products to be used in aerosol form comprising the preparation of a base composition, the introduction of this composition into an aerosol container and the use of a propellant, wherein the composition is previously inoculated with micro-organisms able to bring about a fermentation with the giving off within the container of carbondioxide gas which serves as the propellant.

The invention also has for its object a device equipping the aerosol container and permitting the introduction into the said container, after stabilizing the pressure therein at the end of fermentation, of certain constituents of the product which could interfere with the formation of the micro-organisms.

Figure 1:
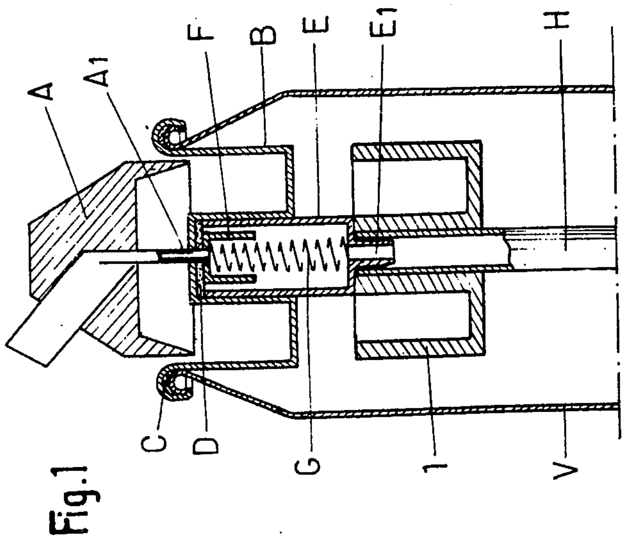
Figure 2:
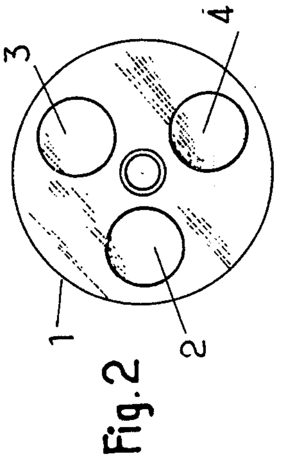

The various features and advantages of the invention can be gathered more clearly from the following description with reference to the drawings, wherein show:

FIG. 1, schematically an aerosol container equipped with a constituent introduction device according to a first embodiment of the invention;

FIG. 2, a schematic plan view thereof;

FIG. 3, a sectional view of a pressurized constituent introduction device in accordance with a variant.

The process forming the object of the invention will be illustrated hereinafter by describing a certain number of non-limitative application examples taken from the cosmetic industry.

| Fatty phase | g |
|---|---|
| Sorbitan monostearate | 15 |
| Hazelnut oil | 30 |
| Sweet almond oil | 30 |
| Isopropyl myristate | 20 |
| Bees-wax | 5 |
| Cetyl alcohol | 10 |

-continued

| Fatty phase | g |
|---|---|
| Antisolar agent | 20 |
| Aqueous phase: | |
| Polyethoxylated sorbitan monostearate | 35 |
| Saccharose | 50 |
| Ammonium sulphate | 0.2 |
| Potassium phosphate | 0.2 |
| Magnesium sulphate | 0.1 |
| Distilled water ad 1000 + a few oligo-elements in a highly diluted solution (Fe, Zn, Mn, Co). | |

The emulsion is prepared in the conventional manner by melting the fatty phase at 65° C and then whilst maintaining this temperature heating the aqueous phase to 65° C and maintaining it at this temperature until the ingredients have dissolved, and by slowly pouring the fatty phase into the aqueous phase accompanied by slow stirring.

Stirring is continued until the temperature has dropped to 32° C, followed by inoculation with kefir grains.

The kefir is in the form of hard translucid grains of irregular shape and variable size (3 to 10 mm). Each of these represents a considerable accumulation of the four specific micro-organisms of kefir, i.e., three bacteria and a yeast. The three bacteria are as follows: *Lactobacillus caucasicus*, *Streptococcus lactis*, and *leuconostoc mesenteroides*, the yeast is *Saccharomyces fragilis*.

The kefir is cultured in per se known manner ensuring that the culture medium is prepared in such a way and renewed every so often so as to obtain a good physiological state of the grains permitting an intense fermentative activity.

1 kg of emulsion is inoculated with 50 g of kefir grains at 32° C, and it is left in contact for 8 hours whilst maintaining this temperature. Propagation of the micro-organisms occurs which leads to a weight increase of the grains, accompanied by a migration of the micro-organisms towards the aqueous phase of the emulsion, where they remain in suspension. By filtering on cloth when the inoculation operation is at an end the kefir grains are separated from the emulsion and can then be re-used. This filtering operation makes it impossible for them to block the aerosol container valve.

During fermentation the pH of the emulsion has a tendency to drop and for adjusting it to the value of 6.5 it is preferable to add to the inoculated and filtered but still not conditioned emulsion an alkaline agent such as triethanol amine which activates fermentation.

The emulsion is then conditioned by introducing the seeded emulsion into aerosol containers by purging the residual volume with nitrogen and then fixing the valve by crimping. The containers are then placed in an incubator at a temperature of 32° C and the development of the pressure resulting from fermentation is followed. This is stabilized at the end of 7 days and measured at a temperature of 25° C, reaches a value of 8 kg. Fermentation is then at an end.

As during fermentation the product has become too acid for cosmetic use and also contains no perfume ( as the latter are harmful to micro-organisms they are not used in the emulsion composition as indicated hereinbefore), after fermentation an alkaline agent (new addition of triethanol amine) should be added, bringing the pH to a desired value. In addition a perfume concentrate should be added. This addition takes place with the device shown in the drawings.

According to a first embodiment (FIGS. 1 and 2) the device is a small ring-shaped receptacle 1, fixed about the upper part of the plunger tube H adjoining the valve, which is itself fixed to the aerosol container V. The latter comprises in per se known manner a valve equipped with a diffuser button A. The valve mechanism is located in a casing E whose end fitting El is attached to the upper end of the plunger tube. A spring-operated cap F houses a spring G and terminates in an atomizer which receives the rod Al of diffuser A. A cap B seals the container and supports both valve and diffuser. A cap joint C and an inner air seal D are provided. The spring-operated cap F ensures the tight sealing of the valve when the diffuser button A is not pressed.

Receptacle 1 either has partitions defining compartments or recesses such as 2, 3, 4 (FIG. 2).

After introducing the inoculated emulsion into the expansion vessel and prior to crimping the valve the perfume and alkaline agent are respectively placed in two of the recesses of receptacle 1. Once fermentation is at an end the aerosol container is inclined or turned upside-down so that these products drop into the emulsion.

In the variant of FIG. 3 a container 5 has an upper end fitting 6 which can be connected to a compressed gas source and a lateral pipe 7 used for the introduction of the additives. This introduction takes place by means of a syringe, after which the pipe 7 is sealed by a plug 8.

Container 5 has a lower end fitting 9 equipped with a member 10 which can be fitted to the atomizer of the spring-operated cap of the valve. In the drawing a female member for fitting to a male atomizer is shown, whereas this member would be male in the case of a female valve.

The example described hereinbefore gives a better understanding of the features of the invention.

The emulsion is prepared in conventional manner prior to inoculation. However, the perfume and any other constituent liable to interfere with micro-organism formation in the inoculated emulsion is eliminated. However, to the conventional composition have been added saccharose and certain mineral salts, ammonium sulphate, potassium phosphate and magnesium sulphate. The saccharose serves as a nutrient agent which is indispensable for the micro-organisms, whilst the mineral salts provide the essential elements (nitrogen, phosphorus, sulphur, magnesium and potassium) necessary for their development.

Oligo-elements have also been added and whilst these are not indispensable they serve as fermentation catalysts.

The emulsifier (polyethoxylated sorbitan monostearate) was chosen from among those which have been found to be non-toxic or only slightly toxic for the micro-organisms.

This emulsion is of the "oil-in-water type." The temperature is brought to 32° C before inoculation, this temperature having proved optimum for the development of the kefir micro-organisms. However, inoculation and fermentation take place at a temperature between 18° and 35° C, whereby the inoculation period varies between 6 to 12 hours depending on whether the temperature is chosen at the top or bottom of this range. Outside this range subsequent fermentation would be incomplete and would not permit adequate pressures to be reached.

The propulsion pressure in the aerosol is obtained through the formation of carbondioxide gas during fermentation. This carbondioxide gas which has a biological origin is produced in situ so that there is no problem of introduction into the aerosol container or of mixing with the product. Moreover, the formation of the micro-organisms which causes fermentation takes place to the detriment of that of all other harmful micro-organisms which could be present. This effect is added to the bactericidal and bacteriostatic power inherent in the carbondioxide gas making a chemical preservative unnecessary. Unlike chemical preservatives, carbondioxide gas (of biological and therefore pure origin) is entirely anallergenic.

A further advantage of the process described results from the fact that yeasts have the property of biosynthesising vitamin B, constituting an interesting element for dermatological products.

Generally the fermentation agent permits the biosynthesis of different biologically active principles (vitamins, enzymes, proteins).

Thus, there is a simultaneous auto-pressurisation, auto-preservation and auto-concentration of a biological type of the inoculated product.

The purging operation which is performed after introducing the product into the aerosol container prevents the production of oxidation reactions.

EXAMPLE 2

Tonic water

The process is the same as for Example 1 but with the following starting formulation:

| | |
|---|---|
| Gentian-blackcurrant infusion each of 5 g/l ad 1000 | |
| Saccharose | 50 g |
| Magnesium sulphate | 0.5 g |
| Potassium phosphate | 0.1 g |
| Ammonium nitrate | 0.2 g |
| Sodium chloride | 0.1 g |

The contact time with kefir for inoculation purposes is reduced to 7 hours because the viscosity of the medium is much lower than in the previous Example.

Fermentation is stopped after 5 days because a stable pressure of 9 kg measured at 25° C has been reached. An alkaline agent (for example, triethanolamine) is then introduced to bring the pH (which reached a value of 3.4 at the end of fermentation) to an adequate value. A perfume concentrate and a dissolving agent permitting the dissolving of the latter are also added.

This introduction can, for example, take place by means of the device shown in FIGS. 1 and 2. Then 0.32 cc of perfume and 0.83 cc of dissolving agent (polyethoxylated alkyl phenol) are placed in one of the recesses of receptacle 1, 0.65 cc of triethanol amine being placed in the other recess. Once the pressure has stabilized and aerosol container is turned upside-down and then agitated to ensure the homogeneity of the mixture.

EXAMPLE 3

Lime blossom shampoo

Two solutions, designated hereinafter by A and B, are prepared separately by simply heating the following mixtures:

| | | |
|---|---|---|
| | (Lime blossom infusion (10 g/l) ad 1000 | |
| | (Saccharose | 50 g |
| | (Ammonium nitrate | 0.2 g |
| Solution A | (Disodium phosphate | 0.1 g |
| | (Magnesium sulphate | 0.05 g |
| | (Potassium chloride | 0.05 g |
| | (40% Sodium lauryl sarcosinate | 100 g |
| Solution B | (30% Triethanol amine lauryl ether sulphate | 150 g |

Solution A only is inoculated with 50 g of kefir per liter and is left in contact for 9 hours at 30° C.

After filtering the pH is adjusted to a value of 6.5 as in Example 1, and then the thus inoculated solution A is introduced into aerosol containers. The containers are placed in an incubator at 30° C and after 5 days the pressure stabilizes at a value of 7 kg measured at 25° C.

By means of the device shown in FIG. 3, 20 cc of the above solution B is then injected into the containers at a pressure which is higher than the internal pressure of the aerosol. Moreover, as in the previous example, a pH correcting agent, a perfume concentrate and a dissolving agent are added by means of the device shown in FIGS. 1 and 2. Agitation takes place to ensure homogeneity.

Solution B contains two surface-active agents necessary for preparing shampoos, but which are liable to impair fermentation, hence they are not added until fermentation is at an end.

EXAMPLE 4

After-shave lotion

The following solutions A and B are prepared separately by simply heating the mixture of their constituents:

| | | |
|---|---|---|
| | (Alcohol at 96° (15° C) | 607.7 cc or 548 g |
| A | (Glycerin | 10 g |
| | (Dissolving agent | 4 g |
| | (Perfume | 10 g |
| | (Saccharose | 30 g |
| | (Exchanged water ad 1 kg | |
| | (Disodium hydrogen phosphate | 0.05 g |
| | (Magnesium sulphate | 0.03 g |
| | (Ammonium nitrate | 0.1 g |
| | (Potassium chloride | 0.03 g |

Solution B only is inoculated with 50 g of kefir per liter and contact is maintained for 8 hours at 32° C. After filtering the pH is adjusted to a value of 6.5 and the thus inoculated solution B is then introduced into aerosol containers.

The containers are placed in an incubator at 32° C and at the end of 8 days the pressure stabilises at 6 kg, measured at 25° C.

By means of the device shown in FIG. 3, 55 cc of Solution A are then injected into the containers at a pressure in excess of the internal pressure of the aerosol. In addition 1 g of allantoin and 0.3 g of triethanol amine are added by means of the device shown in FIGS. 1 and 2. Agitation then takes place to ensure homogeneity.

In particular, solution A contains alcohol and perfume which are incompatible with micro-organism formation and are therefore only added after fermentation.

In the four Examples described hereinbefore the fermentation agent used was a mixture of bacteria and yeasts, being particularly active and easy to culture and use, i.e., kefir, but this only represents an advantageous embodiment of the process. If in general manner yeasts are preferred to bacteria because they only require a relatively simple and therefore relatively cheap culture medium whilst being robust relative to the various constituents of the products and relative to the carbondioxide gas and acidity excess, it is also possible to use, for example, *Saccharamyces cerevisiae*, *Saccharomyces apiculatus* or *Saccharomyces mali.* It is even possible to use successfully certain non-pathogenic anaerobic bacteria preferably chosen from the following species: bacteria such as *Lactobacillus fermenti*, *Lactobacillus pastorianus*, *Lactobacillus bifidus;* micrococci such as *Leuconostoc ectrovorum*, *Leuconostoc dextranicum*, *Leuconostoc mesenteroid;* actinomyces such as *Propionibacterum pentosaceum;* clostridium species such as *Clostridium aceto-butylicum*, *Clostridium saccharobutylicum*, *Clostridium acetonicum*, *Clostridium butylicum*, *Clostridium toanum*, *Clostridium butyricum;* and bacillus species such as *Bacillus acetoethylicus* or *Bacillus polymyxa*.

In each preparation the fermentation agent can be chosen as a function of the desired pressure for the carbondioxide gas propellant and the metabolites which it is desired to biosynthesise.

EXAMPLE 5

Emollient emulsion

| | |
|---|---|
| Lanolin | 40 g |
| Hazelnut oil | 50 g |
| Wheat germ oil | 30 g |
| Glycerol monostearate | 30 g |
| Glycol monostearate | 20 g |
| Stearyl alcohol | 15 g |
| An aqueous phase is prepared containing: | |
| Potassium phosphate | 0.2 g |
| Magnesium sulphate | 0.1 g |
| Ammonium sulphate | 0.1 g |
| Maltose | 40 g |
| Blossom infusion ad 1000 | |
| Polyethoxylated fatty alcohol containing 17 ethylene-oxide molecules | 30 g |

The aqueous phase, heated to a temperature of 65° C, is mixed with the fatty phase which is maintained at the same temperature by slowly pouring the fatty phase into the aqueous phase accompanied by gentle stirring. Stirring is continued until cooling to 30° C takes place. The mixture is then inoculated by introducing 1 g of lyophilized *Saccharomyces cerevisiae* (low fermentation yeast) per 100 g of emulsion at 30°, contact being maintained for 6 hours. After filtering on cloth the pH is adjusted to 6.5.

Conditioning takes place by introducing the emulsion into aerosol containers (80 cc of emulsion are introduced into a container with a total capacity of 115 cc) by purging the residual nitrogen volume and fixing the valves.

The containers are placed in an incubator at 30° C for 8 days. Stabilization of the pressure at a value of 6 kg (measured at 25° C) is then achieved.

By means of the device described hereinbefore an alkaline agent is introduced after fermentation for neutralizing excess acidity. A perfume concentrate is also introduced.

EXAMPLE 6

Astringent lotion

| | |
|---|---|
| Distilled water ad 1000 | |
| Apple juice | 300 g |
| Grape juice | 150 g |
| Glucose | 20 g |
| Potassium phosphate | 0.2 g |
| Magnesium sulphate | 0.1 g |
| Ammonium sulphate | 0.2 g |

Inoculation and conditioning are performed in accordance with the process described in Example 5. The fermentation agent used is *Saccharomyces apiculatus*. The pressure developed by fermentation is stabilized after 8 days, measured at 25° C, and is of the order of 8 to 9 kg. The addition of a pH correcting agent, a perfume and a dissolving agent takes place as described hereinbefore.

EXAMPLE 7

Hydrating emulsion

The aqueous phase of the emulsion is prepared by dissolving in 1 liter of previously filtered potato liquor 10 g of peptone, 30 g of clucose and 2.5 g of asparagine. 30 g of an emulsifier selected from the group of non-ionic surface-active agents resulting from the mixed condensation of propylene and ethylene oxides (HLB 14) are added.

The fatty phase of the emulsion is prepared by melting in the water bath and then intimately mixing the following constituents:

| | |
|---|---|
| Purified lanolin | 20 g |
| Sweet almond oil | 60 g |
| Glycerol monostearate | 50 g |
| Cetyl alcohol | 15 g |

855 g of the aqueous phase are brought to a temperature of 65° C and accompanied by slow but regular agitation 145 g of the fatty phase which has previously been brought to the temperature of 65° C are incorporated therein.

Agitation is continued until cooling to 30° C is obtained.

Inoculation of the emulsion maintained at 30° C takes place by adding 10 cc of a clostridium butyricum suspension in a M/15 phosphate buffer solution of pH 6.9.

After homogenization the emulsion is conditioned as described in the previous Example, stabilization being obtained after 10 days with a pressure value of 4 kg measured at 25° C. The perfume and alkaline agent for neutralising excess acidity are added in accordance with the process described hereinbefore.

EXAMPLE 8

Vitaminized water

| | |
|---|---|
| Ethereal yeast extract | 3 g |
| Speakman saline mixture | 2 g |
| Ammonium sulphate | 0.4 g |
| Glucose | 35 g |
| Hydrolysed casein | 7 g |
| Distilled water ad 1000 | |

Heating takes place to 50° C followed by filtration. Inoculation takes place with a fresh strain (less than 29 hours) of *Clostridium aceto-butylicum* developed on a medium consisting of cereal (wheat and maize) liquor, yeast extract and glucose.

Conditioning takes place as in the previous Example. The inoculation and fermentation temperature is 33° C. Stabilisation is obtained at the end of 8 days, the pressure reached being 6 kg (measured at 25° C).

Perfume, acidity neutralizer and dissolving agent are added after fermentation in the manner indicated hereinbefore.

It is again stressed that the above Examples are not limitative.

In all the Examples an emulsifier has been chosen which does not excessively interfere with fermentation. In general manner, polyethoxylated sorbitan esters, non-ionic surface-active agents resulting from the mixed condensation of ethylene and propylene oxides or polyethoxylated fatty alcohols are preferably chosen. It is stressed that most known emulsifiers are toxic to micro-organisms and consequently a very careful choice must be made. The culture medium necessarily contains a sugar or a substance able to supply a sugar (sugar precursor such as starch). Its composition will vary according to the micro-organisms used as fermentation agents.

What is claimed is:

1. A process for the preparation of products for use in aerosol form comprising the preparation of a base composition, the introduction of this composition into an aerosol container and the use of a propellant, wherein the composition is previously inoculated by organisms able to bring about fermentation with the giving off within the container of carbondioxide gas which serves as the propellant.

2. A process according to claim 1, wherein a sugar or other nutrient medium for the micro-organisms is introduced into the base compositions and wherein all the constituents of the product which are liable to interfere with micro-organism formation are not incorporated into the product until after the pressure has stabilized in the container.

3. A process according to claim 1 wherein a pH correcting agent is introduced.

4. A process according to claim 1, wherein the said micro-organisms contain a yeast.

5. A process according to claim 1 for the preparation of emulsions, wherein the emulsifier is selected from the group of polyethyoxylated sorbitan esters, non-ionic surface-active agents resulting from the mixed and condensation of propylene and ethylene oxides, or fatty polyethoxylated alcohols.

6. A process according to claim 1, wherein the composition is inoculated with kefir, the temperature being maintained at a value between 18° and 35° C, and preferably close to 32° C during inoculation and fermentation, whereby the inoculation operation lasts between 6 and 12 hours, and preferably about 8 hours.

7. A process according to claim 6, wherein at the end of the inoculation operation the composition is filtered to eliminate kefir grains.

8. A process according to claim 2 applied to the preparation of a cosmetic emulsion, wherein a perfume and a pH correcting agent are added after stabilizing the pressure in the aerosol container at the end of several days of fermentation.

9. A process according to claim 2 applied to the preparation of a cosmetic lotion, wherein a perfume, a dissolving agent and a pH correcting agent are added after stabilizing the pressure in the aerosol container at the end of several days of fermentation.

10. A process according to claim 2 applied to the preparation of a shampoo, wherein a perfume, a surface-active agent and a pH correcting agent are added after stabilizing the pressure in the aerosol container at the end of several days of fermentation.

11. A process according to claim 2 applied to the preparation of an alcoholic liquid, wherein the alcohol is added after stabilizing the pressure in the aerosol container at the end of several days of fermentation.

12. A process according to claim 1, wherein micro-organisms selected from the following are used: *Saccharamyces cerevisiae*, *Saccharomyces apiculatus*, *Saccharomyces mali*, *Lactobacillus fermenti*, *Lactobacillus pastorianus*, *Lactobacillus bifidus;* *Leuconostoc ectrovorum*, *Leuconostoc dextranicum*, *Luconostoc mesenteroid;* *Propioni bacterum pentosaceum;* *Clostridium aceto-butylicum*, *Clostridium saccharobutylicum*, *Clostridium acetonicum*, *Clostridium butylicum*, *Clostridium toanum*, *Clostridium butyricum;* *Bacillus acetoethylicus*, *Bacillus polymyxa.*

13. A process according to claim 1, wherein one or several oligo-elements in a high diluted solution are added to the base composition.

* * * * *